(12) United States Patent
Sah et al.

(10) Patent No.: US 7,476,257 B2
(45) Date of Patent: Jan. 13, 2009

(54) METHODS TO ENGINEER STRATIFIED CARTILAGE TISSUE

(75) Inventors: Robert L. Sah, San Diego, CA (US);
Kelvin W. Li, San Diego, CA (US);
Travis J. Klein, San Diego, CA (US);
Barbara L. Schumacher, Cardiff by the Sea, CA (US); Koichi Masuda, Wilmette, IL (US); Eugene J-M. A. Thonar, Lockport, IL (US)

(73) Assignees: Rush University Medical Center, Chicago, IL (US); The Regents of the University of California, Oakland, CA (US)

( * ) Notice: Subject to any disclaimer, the term of this patent is extended or adjusted under 35 U.S.C. 154(b) by 380 days.

(21) Appl. No.: 10/244,035

(22) Filed: Sep. 13, 2002

(65) Prior Publication Data
US 2003/0077821 A1 Apr. 24, 2003

Related U.S. Application Data

(60) Provisional application No. 60/382,438, filed on May 22, 2002, provisional application No. 60/322,888, filed on Sep. 15, 2001.

(51) Int. Cl.
*A61F 2/28* (2006.01)
*A61F 2/02* (2006.01)
(52) U.S. Cl. ............... 623/23.72; 623/11.11; 424/422; 424/93.7
(58) Field of Classification Search ............ 424/93.7; 623/23.63, 915, 919; 435/372

See application file for complete search history.

(56) References Cited

U.S. PATENT DOCUMENTS

| | | | |
|---|---|---|---|
| 4,356,261 A | 10/1982 | Kuettner | |
| 4,642,120 A | 2/1987 | Nevo et al. | |
| 4,673,566 A | 6/1987 | Goosen et al. | |
| 4,846,835 A | 7/1989 | Grande | |
| 4,904,259 A | 2/1990 | Itay | |
| 4,927,761 A | 5/1990 | Reading et al. | |
| 5,041,138 A | 8/1991 | Vacanti et al. | |

(Continued)

FOREIGN PATENT DOCUMENTS

JP 07-505620 6/1995

(Continued)

OTHER PUBLICATIONS

UMBC Tissue Culture Protocols, Mar. 4, 2006, http://web.archive.org/web/20010304040942/http://www.research.umbc.edu/~jwolf/method5.htm.*

(Continued)

*Primary Examiner*—L Blaine Lankford
*Assistant Examiner*—Allison M. Ford
(74) *Attorney, Agent, or Firm*—Foley & Lardner LLP

(57) ABSTRACT

The present invention is directed to a cultured, stratified cartilage tissue that comprises a tissue-engineered, cohesive cartilage construct comprised of two or more cartilage layers, wherein each cartilage layer comprises chondrogenic cells having a chondrocytic phenotype corresponding to chondrocytes present in: a superficial-tangential zone of natural cartilage; a middle-transitional zone of natural cartilage; a deep-radial zone of natural cartilage; or a calcified cartilage zone of natural cartilage.

18 Claims, 3 Drawing Sheets

U.S. PATENT DOCUMENTS

| | | | |
|---|---|---|---|
| 5,053,050 A | 10/1991 | Itay | |
| 5,067,964 A | 11/1991 | Richmond et al. | |
| 5,073,491 A | 12/1991 | Familletti | |
| 5,197,985 A | 3/1993 | Caplan et al. | |
| 5,226,914 A | 7/1993 | Caplan et al. | |
| 5,286,495 A | 2/1994 | Batich et al. | |
| 5,294,446 A | 3/1994 | Schlameus et al. | |
| 5,326,357 A * | 7/1994 | Kandel | 623/23.72 |
| 5,364,580 A | 11/1994 | Prent | |
| 5,368,858 A | 11/1994 | Hunziker | |
| 5,486,359 A | 1/1996 | Caplan et al. | |
| 5,516,532 A | 5/1996 | Atala et al. | |
| 5,536,656 A | 7/1996 | Kemp et al. | |
| 5,538,887 A | 7/1996 | Peindl et al. | |
| 5,541,295 A | 7/1996 | Barrach et al. | |
| 5,549,904 A | 8/1996 | Juergensen et al. | |
| 5,591,740 A | 1/1997 | Chipman et al. | |
| 5,612,028 A | 3/1997 | Sackier et al. | |
| 5,635,390 A | 6/1997 | Peindl et al. | |
| 5,648,099 A | 7/1997 | Batich et al. | |
| 5,667,778 A | 9/1997 | Atala | |
| 5,693,514 A | 12/1997 | Dorian et al. | |
| 5,693,624 A | 12/1997 | Hardy et al. | |
| 5,700,289 A | 12/1997 | Breitbart et al. | |
| 5,700,774 A | 12/1997 | Hattersley et al. | |
| 5,707,962 A | 1/1998 | Chen et al. | |
| 5,709,854 A | 1/1998 | Griffith-Cima et al. | |
| 5,713,374 A | 2/1998 | Pachence et al. | |
| 5,716,404 A | 2/1998 | Vacanti et al. | |
| 5,716,616 A | 2/1998 | Prockop et al. | |
| 5,723,331 A | 3/1998 | Tubo et al. | |
| 5,736,396 A | 4/1998 | Bruder et al. | |
| 5,786,217 A | 7/1998 | Tubo et al. | |
| 5,872,209 A | 2/1999 | Bartnik et al. | |
| 5,902,741 A | 5/1999 | Purchio et al. | |
| 5,908,784 A | 6/1999 | Johnstone et al. | |
| 5,932,459 A | 8/1999 | Sittinger et al. | |
| 5,935,796 A | 8/1999 | Fosang | |
| 6,077,989 A | 6/2000 | Kandel et al. | |
| 6,080,579 A | 6/2000 | Hanley et al. | |
| 6,093,557 A | 7/2000 | Pui et al. | |
| 6,132,976 A | 10/2000 | Poole et al. | |
| 6,143,501 A | 11/2000 | Sittinger et al. | |
| 6,143,744 A | 11/2000 | Broka et al. | |
| 6,159,460 A | 12/2000 | Thompson et al. | |
| 6,187,907 B1 | 2/2001 | Chen et al. | |
| 6,197,061 B1 | 3/2001 | Masuda et al. | |
| 6,197,586 B1 | 3/2001 | Bhatnagar et al. | |
| 6,200,606 B1 | 3/2001 | Peterson et al. | |
| 6,214,369 B1 | 4/2001 | Grande et al. | |
| 6,242,247 B1 | 6/2001 | Rieser et al. | |
| 6,306,169 B1 | 10/2001 | Lee et al. | |
| 6,312,952 B1 | 11/2001 | Hicks, Jr. | |
| 6,316,194 B1 | 11/2001 | Karn et al. | |
| 6,319,712 B1 | 11/2001 | Meenen et al. | |
| 6,451,060 B2 | 9/2002 | Masuda et al. | |
| 6,464,729 B1 * | 10/2002 | Kandel | 623/23.63 |
| 6,465,205 B2 | 10/2002 | Hicks | |

FOREIGN PATENT DOCUMENTS

| | | |
|---|---|---|
| JP | 2001-89390 | 4/2001 |
| JP | 2004 504835 | 2/2004 |
| WO | 94/28889 | 12/1994 |
| WO | WO 97/17430 | 5/1997 |
| WO | WO 98 55594 | 12/1998 |
| WO | WO 00/51527 | 9/2000 |

OTHER PUBLICATIONS

Bentley, "Articular Cartilage Changes in Chondromalacia Patellae", *Journal of Bone and Joint Surgery, British Volume*, 1985, vol. 67 B, No. 4, pp. 769-774.*

Hunter, W. "On the Structure and Diseases of Articulating Cartilage." *Philos Trans R Soc London 42*, pp. 514-521 (1943).

Woessner, J.F. "The Determination of Hydroxyproline in Tissue and Protein Samples Containing Small Proportions of this Amino Acid." *Arch Biochem Biophys 93*, pp. 440-447 (1961).

Scott, et al., "Differential Staining of Acid Glycosaminoglycans (Mucopolysaccharides) by Alcian Blue in Salt Solutions." *Histochemie 5*, pp. 221-233 (1965).

Klagsburn, "Large Scale Preparation of Chondrocytes," *Methods Enzymol 58*, pp. 560-564 (1979).

Maroudas, A. "Adult Articular Cartilage.", (*ed. Freeman, M.A.R.*) Pitman Medical, Tunbridge Wells, England; pp. 215-290, 1979).

Lee, et al., "Oscillatory Compressional Behavior of Articular Cartilge and Its Associated Electromechanical Properties." *J Biomech Eng 103*, pp. 281-292 (1981).

Pal, et al., "Structural Changes During Development in Bovine Fetal Epiphyseal Cartilage." *Collagen Rel Res 1*, pp. 151-176 (1981).

Mankin, J.J. "The Response of Articular Cartilage to Mechanical Injury". *J Bone Joint Surg 64-A*, pp. 460-466 (1982).

Hascall, et al., "Biosynthesis and Turnover of Proteoglycans in Organ Culture of Bovine Articular Cartilage." *J Rheum Suppl 11*, pp. 45-52 (1983).

Farndale, et al., "Improved Quantitation and Discrimination of Sulphated Glycosaminoglycans by Use of Dimethylmethylene Blue." *Biochim Biophys Acta 883*, pp. 173-177 (1986).

Mizrahi, et al., "The "Instantaneous" Deformation of Cartilage: Effects of Collagen Fiber Orientation and Osmotic Stress." *Biorheology 23*, pp. 311-330 (1986).

Fernandez, et al., "The Structure of Anchorin CII, a Collagen Binding Protein Isolated from Chondrocyte Membrane." *J Bio Chem 363* (12) pp. 5921-5925 (1987).

Frank, et al., "Cartilage Electromechanics—II. A Continuum Model of Cartilage Electrokinetics and Correlation with Experiments." *J Biomech 20* (6) pp. 629-639 (1987).

Freshney, "Culture of Animal Cells: A Manual of Basic Techniques." $2^{nd}$ ed., *A.R. Liss Inc.*, New York, pp. 137-168 (1987).

Aydelotte, et al., "Differences Between Sub-Populations of Cultured Bovine Articular Chondrocytes II. Proteoglycan Metabolism." *Connect Tissue Res 18*, pp. 223-234 (1988).

Aydelotte, et al., "Differences Between Sub-Populations of Cultured Bovine Articular Chondrocytes,I. Morphology and Cartilage Matrix Production." *Connect Tissue Res 18*, pp. 205-222 (1988).

Kim, et al., "Fluorometric Assay of DNA in Cartilage Explants Using Hoechst 33258." *Anal Biochem 174*, pp. 168-176 (1988).

Caplan. "Cell and Molecular Strategies for Massive Bone Repair/Regeneration." *J Jpo Orthop Assoc 63* (4) (1989).

Grande, et al., "The Repair of Experimentally Produced Defects in Rabbit Articular Cartilage by Autologous Chondrocyte Transplantation." *J Ortho Res 7*, pp. 208-218 (1989).

Morales, et al., "Effects of Interleukin-1 and Lipopolysaccharides on Protein and Carbohydrate Metabolism in Bovine Articular Cartilage Organ Cultures." *Conn Tissue Res 19*, pp. 255-275 (1989).

Johnson, et al., "The Early Response to Articular Cartilage to ACL Transection in a Canine Model." *Exp Pathol 38*, pp. 37-52 (1990).

Kempson. "Age-Related Changes in the Tensile Properties of Human Articular Cartilage: a Comparative Study Between the Femoral head of the Hip Join and the Talus of the Ankle Joint." *J Biochem Biophys Acta 1075*, pp. 223-230 (1991).

Hauselmann, et al., "Synthesis and Turnover of Proteoglycans by Human and Bovine Adult Articular Chondrocytes Cultered in Alginate Beads." *Matrix 12*, pp. 116-29 (1992).

Hunziker, E.B. "Articular Cartilage Structure in Humans and Experimental Animals" (ed. Kuettner, et al.) pp. 183-199 (Raven Press, New York, 1992).

Kwan, et al., "The Effect of Storage on the Biomechanical Behavior of Articular Cartilage—A Large Strain Study." *J Biomech Eng 114*, pp. 149-153 (1992).

Wu, et al., "Identification of Cross-Linking Sites in Bovine Cartilage Type IX Collagen Reveals an Antiparallel Type II-Type IX Molecular Relationship and Type IX to Type IX Bonding." *J Biol Chem 267* (32) pp. 23007-23014 (1992).

Knudson. "Hyaluronan Receptor-Directed Assembly of Chondrocyte Pericellular Matrix." *J Cell Biology 120*(3), pp. 825-834 (1993).

Ratcliffe, et al. "In Vivo Effects of Naproxen on Composition, Proteoglycan Metabolism and Matrix Metalloproteinase Activities in Canine Articular Cartilage." *J Ortho Res 11*, pp. 163-171 (1993).

Buckwater, et al., "Structural Differences Between Two Populations of Articular Cartilage Proteoglycan Aggregates." *J Ortho Res 12*, pp. 144-148 (1994).

Guilak, et al., "Mechanical and Biochemical Changes in the Superficial Zone of Articular Cartilage in Canine Experimental Osteoarthritis." *J of Ortho Res 12*, pp. 474-484 (1994).

Hauselmann, et al., "Phenotypic Stability of Bovine Articular Chondrocytes After Long-Term Culture in Alginate Beads." *J Cell Sci 107* (1), pp. 17-27, Essex, GB (1994).

Hendrickson, et al., "Chondrocyte-Fibrin Matrix Transplants for Resurfacing Extensive Articular Cartilage Defects." *J Orth Res 12*, pp. 485-497 (1994).

MacGinitie, et al., "Electric Field Stimulation Can Increase Protein Synthesis in Articular Cartilage Explants." *J Ortho Res 12*, pp. 151-160 (1994).

Mok, et al., "Aggrecan Synthesized by Mature Bovine Chondrocytes Suspended in Alginate. Identification of Two Distinct Metabolic Matrix Pools." *J Biol Chem 269*, 33021-7 (1994).

Schumacher et al., "A Novel Proteoglycan Synthesized and Secreted by Chondrocytes of the Superficial Zone of Articular Cartilage.", *Arch Biochem Biophys 311*, pp. 144-152 (1994).

Setton, et al., "Mechanical Properties of Canine Articular Cartilage Are Significantly Altered Following Transection of the Anterior Cruciate Ligament." *J of Ortho Res 12*, pp. 451-463 (1994).

Wakitani, et al., "Mesenchymal Cell-Based Repair of Large, Full-Thickness Defects of Articular Cartilage." *J Bone Joint Surg 76*, pp. 579-591 (1994).

Masuda, et al., "Age-Related Differences in the Metabolism of Hyaluroman Present in Two Distinct Compartments of the Matrix Formed by Articular Chondrocytes In Vitro." $41^{st}$ *Annual Meeting, Orthopaedic Research Society*, Feb. 13-16, Orlando, Florida (1995).

Sah, et al., "Tissue Engineering of Articular Cartilage." *Curr Opin Orthop 6*, pp. 52-60 (1995).

Aydelotte, et al., "Effects of Misoprostol with Interleukin-1 on Proteoglycan Metabolism of Cultured Articular Chondrocytes." *Am J Ther 3*, pp. 3-8 (1996).

Hauselmann, et al., "Adult Human Chondrocytes Cultured in Alginate Form a Matrix Similar to Native Human Articular Cartilage." *Am J Physiol 271* (3 Pt 1), pp. C742-C752 (1996).

Hauselmann, et al., "The Superficial Layer of Human Articular Cartilage is More Susceptible to Interleukin-1-Induced Damage than the Deeper Layers.", *Arthritis Rheum 39*, (3) pp. 478-488, Mar. 1996.

Petit, et al., "Characterization of Crosslinked Collagens Synthesized by Mature Articular Chondrocytes Cultured in Alginate Beads: Comparison of Two Distinct Matrix Compartments." *Experimental Cell Res 225*, pp. 151-161 (1996).

Sah, et al., "Differential Effects of Serum, Insulin-like Growth Factor I, and Fibroblast Growth Factor-2 op the Maintenance of Cartilage Physical Properties During Long-Term Culture." *J of Ortho Res 14*, pp. 44-52 (1996).

Shakibaei, et al., "Differentiation of Mesenchymal Limb Bud Cells to Chondrocytes in Alginate Beads." *Cell Biol International* 21, No. 2, pp. 75-86 (1996).

Chiba, et al., "Metabolism of the Extracellular Matrix Formed by Intervertebral Disc Cells Cultured in Alginate." *Spine 22*, No. 24 (1997).

Huch, et al., "Effects of Recombinant Human Osteogenic Protein 1 on the Production of Proteoglycan, Prostaglandin $E_2$, and Interleukin-1 Receptor Antagonist by Human Articular Chondrocytes Cultured in the Presence of Interleukin-1β." *Arth & Rheum 40*, No. 12 (1997).

Martel-Pelletier, et al., "Effects of Aceclofenac and Diclofenac on Synovial Inflammatory Factors in Human Osteoarthritis." *Clin Drug Invest 14* (3), pp. 226-232.

Ririe, et al., "Produce Differentiation by Analysis of DAN Melting Curves during the Polymerase Chain Reaction." *Analytical Biochem 245*, pp. 154-160 (1997).

Schinagl, et al., "Depth-Dependent Confined Compression Modulus of Full-Thickness Bovine Articular Cartilage." *J Orthop Res 15*, pp. 499-506 (1997).

Chen, et al., "Inhomogeneous and Strain-Dependent Electromechanical Properties of Full-Thickness Articular Cartilage." $44^{th}$ *Annual Meeting, Orthopaedic Research Society*, Mar. 16-19, New Orleans, LA (1998).

Chiba, et al., "A New Culture System to Study the Metabolism of the Intervertebral Disc In Vitro." *Spine 23* (17) pp. 1821-1828 (1998).

Namba, et al., "Spontaneous Repair of Superficial Defects in Articular Cartilage in a Fetal Lamb Model." *J Bone Joint Surg 80-A*, pp. 4-10 (1998).

Chen, et al., "Biomechanical Properties of Tissue-Engineered Carilage Synthesized Using the "Alginate-Recovered-Chrondrocytes" (ARC) Method." *Presented at the Molecular Cell Biology of Cartilage Development and Repair Conference*, California, Jun. 2-6, 1999.

Flannery, et al.,, "Articular Cartilage Superficial Zone Protein (SZP) Is Homologous to Megakaryocyte Stimulating Factor Precursor and Is a Multifunctional Proteoglycan with Potential Growth-Promoting, Cytoprotective, and Lubricating Properties in Cartilage Metabolism. ", *Biochemical and Biophysical Research Communications 254*, pp. 535-541, (1999).

Masuda K, et al., :A Novel Two Step-Method for the Formation of Cartilage Tissue (Alginate Recovered-Chondrocyte Method: ARC Method). *International Symposium on Molecular Cell Biology of Cartilage Development and Repair*, Jun. 2-6, 1999.

Masuda, et al., "The Alginate Recovered-Chondrocyte (ARC) Method for the Formation of Cohesive Cartilaginous Tissue for Articular Cartilage Repair." *International Symposium on Molecular Cell Biology of Cartilage Development and Repair 70* (1999).

Saito, et al., "Dexamethasone Inhibits Collagen Degradation Induced by the Combination of Interleukin-1 and Plasminogen in Cartilage Explant Culture." *Biol Pharm Bull 22* (7) pp. 727-730 (1999).

Schumacher, et al., "Immunodetection and Partial cDNA Sequence of the Proteoglycan, Superficial Zone Protein, Synthesized by Cells Lining Synovial Joints.", *J Orthop Res 17*, pp. 110-120 (1999).

Vunjak-Novakovic, et al., "Bioreactor Cultivation Conditions Modulate the Composition and Mechanical Properties of Tissue-Engineered Cartilage." *J Orthop Res 17*, pp. 130-139 (1999).

Matsumoto, et al., "Tissue Engineered Intervertebral Disc: Enhancement of Formation with Osteogenic Protein-1." $2^{nd}$ *Internantional Conference on Bone Morphogenetic Proteins 2000*, Jun. 7-11, 2000.

Reid, et al. "Cell Attachment, Collagen Binding, and Receptor Analysis on Bovine Articular Chondrocytes." *J Orthop Res 18*, pp. 364-373 (2000).

Wren, et al., "Mechanobiology of Tendon Adaptation to Compressive Loading Through Fibrocartilaginous Metaplasia." *J Rehab Res and Devel. 37* (No. 2), pp. 135-143 (2000).

Wren, et al., "Tendon and Ligament Adaptation to Exercise, Immobilization, and Remobilization." *J of Rehab Res and Devel 37* (No. 2) pp. 217-224 (2000).

Chen et al., "Depth- and Strain-Dependent Mechanical and Electromechanical Properties of Full-Thickness Bovine Articular Cartilage in Confined Compression." *J Biomechanics 34*, pp. 1-12 (2001).

Chen, et al., Depth- and Strain-Dependent Mechanical and Electromechanical Properties of Full-Thickness Bovine Articular Cartilage in Confined Compression. *J Biomechanics 34*, pp. 1-12 (2001).

DiMicco, et al., "Integrative Cartilage Repair: Adhesive Strength Correlates with Collagen Deposition." *J Orthop Res 19*, pp. 1105-1112 (2001).

Matsumoto, et al., "Formation of Transplantable Disc-Shaped Tissues by Nucleus Pulposus and Annulus Fibrosus Cells: Biochemical and Biomechanical Properties." *47th Annual Meeting, Orthopaedic Research Society*, Feb. 25-28, San Francisco, CA (2001).

Pfister, et al., "Del1: A New Protein in the Superficial Layer of Articular Cartilage.", *Biochemical and Biophysical Research Communications 286*, pp. 268-273, (2001).

Rowan. "Cartilage Catabolism in Arthritis: Factors that Influence Homeostasis." *Expert Reviews in Molecular Medicine*. Jul. 2001.

Sah, et al., "Articular Cartilage Repair." *Arthritis and Allied Conditions. A Textbook of Rheumatology*, (Koopman, W.J: ed.) 14th ed. Philadelphia: Lippicott Williams & Wilkins, pp. 2264-2278 (2001).

Schmid, et al., "Superficial Zone Protein (SZP) From Human Cartilage Has Lubrication Activity." *47th Annual Meeting, Orthopaedic Research Society*, Feb. 25-28, San Francisco, California (2001).

Sun, et al., "Characterization of Nucleus Pulposus-Like Tissue Formed In Vitro." *J of Ortho Res 19*, pp. 1078-1084 (2001).

Budsberg, et al., "The Science of Articular Cartilage and Its Deterioration During Osteoarthritis." *Pfizer Animal Health* (2002).

DiMicco, et al., "Integrative Articular Cartilage Repair: Dependence on Developmental Stage and Collagen Metabolism." *Osteoarthritis Cartilage 10*, pp. 218-225 (2002).

Masuda, et al., "A Novel Two-Step Method for the Formation of Tissue-Engineered Cartilage by Mature Bovine Chondrocytes: The Alginate-Recovered-Chondrocyte (ARC) Method." J Orho Res 21, pp. 139-148 (2003).

Thompson, et al., "Coated Biomaterials, Zonal Cell-Seeding and Cartilage Tissue Engineering." *48th Annual Meeting of the Orthopaedic Research Society*, Poster No. 0477.

Translation of Notice of Rejection issued for Japanese Patent Application No. 2003-528559 dated Jun. 2, 2006.

\* cited by examiner

METHODS TO ENGINEER STRATIFIED CARTILAGE TISSUE

This application claims priority to U.S. patent applications Ser. No. 60/322,888, filed Sep. 15, 2001 and 60/382,438, filed May 22, 2002, the entire contents of both of which are hereby entirely incorporated by reference.

STATEMENT REGARDING FEDERALLY SPONSORED RESEARCH

This invention was made with government support under Grant Number BES-9987353 awarded by the National Science Foundation. The government has certain rights in the invention.

FIELD OF INVENTION

The present invention relates to bioengineered cartilage tissues. More particularly this invention relates to stratified engineered cartilage tissue which closely replicates natural cartilage tissue and systems and methods for its use.

BACKGROUND OF THE INVENTION

Cartilage is a complex avascular tissue that is organized into several distinct layers or zones, the superficial zone, middle zone, deep zone and a calcified cartilage zone, each of which is made up of chondrocyte cells surrounded by extracellular matrix. The composition of the extracellular matrix varies by zone but is composed mainly of collagens type II, IX, XI, proteoglycans and water. Although chondrocytes make up less than five percent of the volume of adult cartilage, they are responsible for producing and maintaining the extra-cellular matrix and thus proper joint function. As there is no blood supply to the cartilage matrix, cartilage has a limited ability to heal once damaged and often undergoes degenerative pathological changes. Effectively treating cartilage injuries is further complicated because a complete understanding of the mechanisms and natural history of cartilage injuries and the healing and regeneration of injured cartilage is lacking.

This lack of knowledge has both large human and economic costs because cartilage damage affects millions of people every year in the United States alone. Several hundred thousand people suffer injuries to articular cartilage in major joints, mainly due to sports injuries. It is also estimated that 50 million Americans suffer from osteoarthritis, a painful and debilitating disease that attacks the cartilage in joints.

Several attempts have been made to restore cartilage. Efforts to restore cartilage or promote cartilage repair have been largely unsuccessful for several reasons.

Current methods of surgical restoration of articular cartilage fall into three categories: (1) stimulation of fibrocartilaginous repair; (2) osteochondral grafting; and (3) autologous chondrocyte implantation. Several surgical techniques have been developed to promote the formation of fibrocartilage in areas of cartilage damage. These include subchondral drilling, abrasion, and microfracture. The concept of these procedures is that penetration of the subchondral bone allows chondroprogenitor cells from the marrow to migrate into the defect and effect repair. However, the cartilage produced by this procedure is fibrocartilage, which has relatively poor mechanical properties and does not reproduce the complex physical and chemical properties of articular cartilage.

In osteochondral grafting, articular cartilage is harvested with a layer of subchondral bone and implanted into the articular defect. Fixation of the graft to the host is accomplished through healing of the graft bone to the host bone. The major disadvantages of this technique are donor-site morbidity (in the case of autograft) and risk of disease transmission (in the case of allograft). Additionally, tissue rejection can occur with allografts which compromises the surgical result. Osteochondral allografts are also generally reserved for larger areas of damage extending deep into the subchondral bone.

Autologous chondrocyte implantation is a method of cartilage repair that uses isolated chondrocytes. Clinically, this is a two-step treatment in which a cartilage biopsy is first obtained and then, after a period of ex vivo processing, cultured chondrocytes are introduced into the defect. During the ex vivo processing, the extra-cellular matrix (ECM) is removed and the chondrocytes are cultured under conditions that promote cell division. Once a suitable number of cells are produced, they are implanted into the articular defect. Containment is provided by a patch of periosteum which is sutured to the surrounding host cartilage. The cells attach to the defect walls and produce the ECM in situ. Difficulties with restoration of articular cartilage by this technique fall into three categories: cell adherence, phenotypic transformation, and ECM production. The success of implantation of individual cells (without ECM) is critically dependent upon the cells attaching to the defect bed. Cartilage ECM has been shown to have anti-adhesive properties, which are believed to be conferred by small and large proteoglycans. In vivo studies have shown that only 8% of implanted chondrocytes remain in the defect bed after implantation in rabbits. During the process of expanding the cell population in vitro, chondrocytes usually undergo phenotypic transformation or dedifferentiation. After injection of the cells, the graft construct is incapable of bearing load and must be protected from weight bearing for several weeks to months and the overall recovery period from this form of treatment is 9-12 months.

Other attempts have been made to produce artificial cartilage which can be used to replace or repair natural cartilage. Each of the current methods of cartilage repair has substantial limitations. As a result, several laboratory approaches to production of cartilage tissue in vitro have been proposed. These generally involve seeding of cultured cells (either chondrocytes or pluripotential stem cells) into a biological or synthetic scaffold. The major drawbacks of this type of approach are: (1) difficulty in attaining or maintaining the chondrocyte phenotype; (2) unknown biological effects of the scaffold material on the implanted and native chondrocytes and other joint tissues; and (3) limited attachment of the engineered tissue construct to the defect bed. Likewise these approaches utilize a homogenous population of chondrocytes isolated generically from cartilage tissue and do not accurately imitate the layered structure or function of natural cartilage.

Accordingly, there continues to be a need for cartilage tissue which accurately mimics natural articular cartilage.

SUMMARY OF THE INVENTION

The present invention provides a cultured, stratified cartilage tissue that includes a tissue-engineered, cohesive cartilage construct comprised of two or more cartilage layers. Each cartilage layer contains chondrogenic cells having a chondrocytic phenotype corresponding to chondrocytes present in:
(i) a superficial-tangential zone of natural cartilage;
(ii) a middle-transitional zone of natural cartilage;
(iii) a deep-radial zone of natural cartilage; or
(iv) a calcified cartilage zone of natural cartilage.

In some embodiments, the chondrogenic cells are chondrocytes obtained from the natural cartilage zone which corresponds to the chondrocytic phenotype.

In some of the cartilage constructs the cohesive cartilage construct includes a first layer comprised of chondrogenic cells having the chondrocytic phenotype of chondrocytes in the superficial-tangential zone adjacent to a second layer comprised of chondrogenic cells having the chondrocytic phenotype of chondrocytes in the middle-transitional zone. In others the cohesive cartilage construct is made up of at least a first layer comprised of chondrogenic cells having the chondrocytic phenotype of chondrocytes in the superficial-tangential zone, a second layer comprised of chondrogenic cells having the chondrocytic phenotype of chondrocytes in the middle-transitional zone and a third layer comprised of chondrogenic cells having the chondrocytic phenotype of chondrocytes in the deep-radial zone further wherein the first layer is adjacent is second layer and the second layer is adjacent the third layer. In still others the cohesive cartilage construct includes a first layer comprised of chondrogenic cells having the chondrocytic phenotype of chondrocytes in the middle-transitional zone adjacent to a second layer comprised of chondrogenic cells having the chondrocytic phenotype of chondrocytes in the deep-radial zone. The engineered cohesive cartilage described herein does not need to be supported by a solid support. In the above engineered cartilage each layer can further include a chondrogenic cell-associated matrix corresponding to cartilage matrix present in the cartilage zone with which the chondrocytic phenotype is associated. The cell-associated matrix of the cartilage can correspond to immature cartilage or mature cartilage. In some embodiments one of the layers can have chondrogenic cells having the chondrocytic phenotype of chondrocytes in the superficial-tangential zone which secrete superficial zone protein.

The present invention also provides an engineered cartilage tissue made up of at least a first cartilage layer containing chondrocytes, wherein substantially all of the chondrocytes in the at least first cartilage layer possess the same chondrocytic phenotype. This engineered cartilage tissue can also include one or more successive cartilage layers containing chondrocytes, wherein substantially all of the chondrocytes in each individual successive cartilage layer possess the same chondrocytic phenotype. The chondrocytes in the first cartilage layer can possess a chondrocytic phenotype distinct from the chondrocytes in the successive cartilage layers.

The present invention also provides a method of producing a stratified cartilage tissue that involves culturing a first group of chondrogenic cells with a first chondrogenic phenotype with one or more additional groups of chondrogenic cells having an additional chondrogenic phenotype to produce a tissue-engineered, cohesive cartilage construct having two or more cartilage layers. The chondrogenic phenotypes can correspond to: (i) a superficial-tangential zone of natural cartilage; (ii) a middle-transitional zone of natural cartilage; (iii) a deep-radial zone of natural cartilage; or (iv) a calcified cartilage zone of natural cartilage. The present methods can further comprise one or more of culturing the first group of chondrogenic cells to produce a first cell-associated matrix containing the first group of chondrogenic cells; and culturing the one or more additional groups of chondrogenic cells to produce one or more additional cell-associated matrices containing the one or more additional groups of chondrogenic cells, wherein each of the one or more additional groups of chondrogenic cells produces a cell-associated matrix specific to that group of chondrogenic cells. These steps can be performed in any suitable medium, such as an alginate medium.

The chondrogenic cells can also be cultured on a semipermeable membrane, in the presence of one or more growth factors or both. In some embodiments, the first group of chondrogenic cells and the one or more additional groups of chondrogenic cells are isolated from a natural cartilage zone with which their phenotype is associated. These zones can include superficial-tangential zone chondrocytes, middle-transitional zone chondrocytes, deep-radial zone chondrocytes, or calcified cartilage zone chondrocytes. After the cartilage construct is produced it can be implanted into a joint, such as occurs in the repair of a cartilage defect.

The present methods can also involve contacting one or more test agents with one or more cells or tissues selected from the group consisting of: (a) the first group of chondrogenic cells; (b) the one or more additional groups of chondrogenic cells; (c) the first group of chondrogenic cells with cell-associated matrix; (d) the one or more additional groups of chondrogenic cells with cell-associated matrices; and (e) the tissue-engineered, cohesive cartilage construct. Generally these methods will involve measuring the effect the one or more test agents has on the contacted cells or tissue. Test agents having desirable properties can then be identified and produced as a therapeutic drug.

The present invention also provides kits for producing the present cartilage tissue and carrying out the present methods. The kits generally include instructions and one or more reagents.

Objects and advantages of the present invention will become more readily apparent from the following detailed description.

DETAILED DESCRIPTION OF PREFERRED EMBODIMENTS

Figure 1:
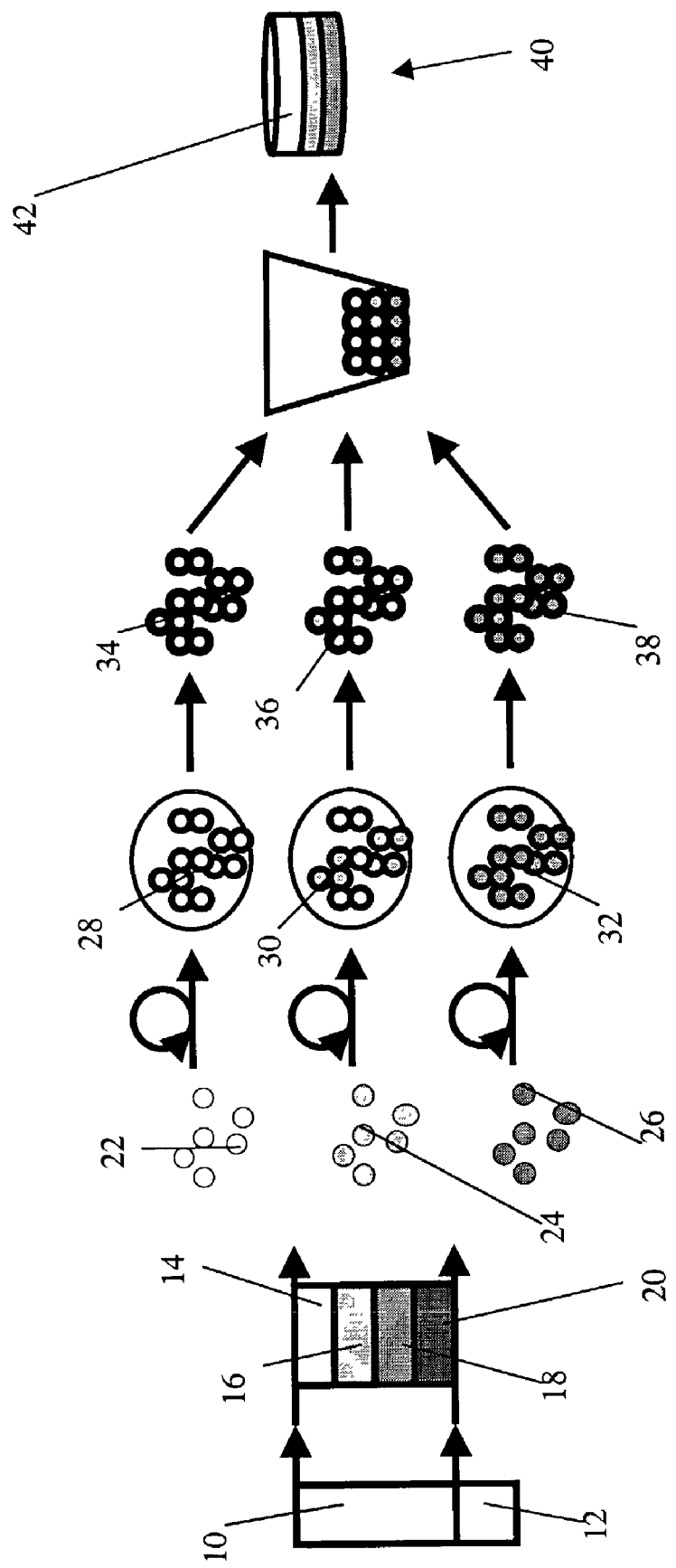
FIG. 1 is a schematic representation depicting the production of engineered cartilage tissue according to the present invention.

One embodiment of the present invention provides an engineered cartilage tissue comprised of two or more layers which mimics the physical zoned structure of natural cartilage, and in particular articular cartilage. In this embodiment, the engineered cartilage is a cohesive piece of tissue where each layer in the engineered cartilage includes chondrogenic cells having a phenotype (i.e. characteristics) for chondrocytes which occur in a natural cartilage zone, i.e., a superficial-tangential zone phenotype, a middle-transitional zone phenotype, a deep-radial zone phenotype or a calcified cartilage zone phenotype. Preferably, the phenotypes of the chondrogenic cells in each layer is different. In other preferred embodiments, one of the outer layers of the tissue secretes superficial zone protein, developmental endothelial locus-1 (Del1) protein, and/or other proteins that help provide joint lubrication.

Another embodiment of the present invention provides a cartilage tissue made up of at least one cartilage layer containing chondrocytes. In some embodiments, substantially all of the chondrocytes in the at least one cartilage layer possess the same chondrocytic phenotype. As used herein, the phrase "substantially all of the chondrocytes possess the same chondrocytic phenotype," or the like, means that the chondrocytes in the cartilage layer are enriched for a single, specific phenotype above the levels that can be obtained by culturing a homogenized sample of cartilage tissue, which is generally derived from full-thickness cartilage. One skilled in the art will recognize that any layer can include chondrocytes isolated from, or having the phenotype of, more than zone of naturally occurring cartilage. Where a mixture of chondrocytes having different phenotypes are used, the cartilage layer as a whole will preferably have a dominant phenotype characteristic of one of the layers of naturally occurring cartilage. For example, where a mixture of superficial and middle zone chondrocytes are present in the same layer, the layer can resemble the superficial zone of cartilage more than the middle zone, or vice versa, depending upon the ratio of superficial or middle zone chondrocytes present in the layer. In some embodiments, greater than 50 percent of chondrocytes in any given layer have the characteristics for the same zonal phenotype. In further embodiments, greater than about 60, 65, 70, 75, 80, 85, 90, 95 or 99 percent of chondrocytes in any given layer have the phenotype of chondrocytes for one specific cartilage zone. Accordingly, about 40, 35, 30, 25, 20, 15, 20, 5 or 1 percent of the chondrocytes in any given layer can have one or more phenotypes that are different than the phenotype of cartilage zone primarily represented by that cartilage layer. Different cartilage layers can also have different percentages of chondrocytes having the same phenotype as compared to other layers.

The engineered cartilage tissue can be made up of as many layers as desired, such as two, three or four layers. Preferably, the cartilage tissue replicates the natural zoned structure of cartilage. In other preferred embodiments, the present invention comprises at least one outer layer that mimics the superficial-tangential zone and has the phenotypic characteristics of high tensile strength, SZP and/or Del1 secretion. For example, when two engineered cartilage layers are present, one layer contains superficial-tangential phenotypic chondrocytes adjacent to a second layer containing middle-transitional phenotypic chondrocytes, one layer has middle-transitional phenotypic chondrocytes and an adjacent layer has deep-radial zone phenotypic chondrocytes, or one layer includes deep-radial zone phenotypic chondrocytes and an adjacent layer includes calcified cartilage zone phenotypic chondrocytes. When three layers of engineered cartilage are present one layer can contain superficial-tangential phenotypic chondrocytes adjacent to a second layer containing middle-transitional phenotypic chondrocytes which is itself adjacent to a third layer containing deep-radial zone phenotypic chondrocytes. Likewise, one layer can include middle-transitional phenotypic chondrocytes adjacent to a second layer, which includes deep-radial zone phenotypic chondrocytes, which is adjacent to a third layer that includes calcified cartilage zone phenotypic chondrocytes. When four layers are present in the engineered tissue, the first layer can contain superficial-tangential phenotypic chondrocytes, a second layer containing middle-transitional phenotypic chondrocytes sandwiched between the first layer and a third layer which includes deep-radial zone phenotypic chondrocytes sandwiched between the second layer and an adjacent fourth layer that includes calcified cartilage zone phenotypic chondrocytes.

Although the above examples illustrate engineered tissues which mimic the order of the zones in natural cartilage, the present engineered tissue is not so limited and all possible combinations of cartilage layers containing the different chondrocytic phenotypes is envisaged. For example a layer containing superficial-tangential zone phenotypic chondrocytes can be adjacent to a layer containing deep-radial zone phenotypic chondrocytes or calcified cartilage zone phenotypic chondrocytes. Likewise, the present engineered tissues are not limited to having a maximum number of cartilage layers.

In another embodiment, each of the engineered tissue layers can further comprise a matrix associated with the chondrogenic cells which is specific to the phenotype of the chondrogenic cells in that layer so that each successive layer also has its own distinct cell-associated matrix specific to the chondrogenic cells in that layer.

Articular cartilage is a hydrated connective tissue which, after skeletal maturity, is composed of a relatively small number and volume (~2-5%) of cells within a fluid-filled extracellular matrix. The molecular components of the extracellular matrix appear to be predominantly responsible for the functional biomechanical properties of the tissue. The sulfated proteoglycan, aggrecan, provides the tissue with a high density of sulfate and carboxyl moieties which are ionized and give the tissue the propensity to swell and resist compression and consolidation. Aggrecan monomers consist of a core protein to which are attached the polyanionic glycosaminoglycan (GAG) chains, chondroitin sulfate and keratan sulfate. These monomers are stabilized by a non-covalent interaction with link protein and a hyaluronan (HA) backbone. In contrast, the cross-linked collagen meshwork resists the swelling tendency of the proteoglycan, and provides tissue integrity and tensile strength. The trifunctional crosslink, hydroxylysylpyridinoline (HP), is formed by a sequence of reactions including post-translational hydroxylation of selected lysine residues of collagen.

The composition, structure and function of articular cartilage vary both with depth from the articular surface to the subchondral bone and is typically described as having sequential zones, superficial, middle, deep, and calcified. In normal adult articular cartilage, the water content and cellularity decrease with depth from the articular surface, while the sulfated GAG content generally increases with depth. The depth-variation in GAG is associated with variations in the relative proportions of chondroitin-4-sulfate, chondroitin-6-sulfate, and keratan sulfate. While the collagen content is approximately constant, both the cells and collagen fibrils of the superficial zone are oriented parallel to the articular surface (i.e., tangential), while the collagen fibrils and cells of the deep zone are oriented perpendicular ("radial") to the surface. The confined compressive modulus is low at the articular surface and increases with depth, whereas the tensile modulus, and strength, decrease with depth from the articular surface. The depth-varying architecture of articular cartilage is critical to its biomechanical function. Compression of the relatively soft superficial region of cartilage improves the congruence between joint surfaces, reduces stress concentrations, and maintains joint lubrication. The high tensile and cohesive properties of the collagen meshwork in the superficial zone helps to maintain tissue integrity and resist wear.

Although generically, homogenized articular cartilage tissue is made up primarily of aggrecan, collagen types II, IX and XI, and hyaluronan, with minimal amounts of type I collagen, the proportions of these components vary depending on the zone of cartilage tested. In addition, the thickness of articular cartilage changes from joint to joint and is generally in the range of 2-4 mm. The present engineered cartilage can closely track these physical and compositional changes.

Preferably, the present engineered cartilage also resembles one or more characteristics of the physical makeup of natural articular cartilage as follows. In natural articular cartilage the superficial-tangential zone is about 10 to 20 percent of the thickness of the cartilage, although it is the most cellular zone. Phenotypically, the chondrocytes in this zone are oblong with their long axis parallel to the articular surface. Chondrocytes in the superficial-tangential zone secrete also SZP, which helps lubricate the joint, and Del1. The cell-associated matrix in this zone is made up primarily of fine, densely packed collagen fibrils organized parallel to the articular surface and has the lowest concentration of proteoglycan and the highest collagen concentration, relative to the other zones. The superficial zone also tends to be the softest zone as deeper cartilage zones can be about twenty five times stiffer than superficial zone cartilage. In further detail, the superficial-tangential zone is made up of two sub-zones, a more superficial layer of a fibrilar sheet/lamina splendens which is a clear film mainly made of a sheet of small fibrils with little polysaccharide and few, if any cells, and a second, cellular layer with flattened chondrocytes. The superficial-tangential zone is the first to show the effects of osteoarthritis. The middle-transitional zone typically makes up about 40 to 60 percent of the cartilage thickness. The collagen fibrils in the middle-transitional zone generally have much larger diameters and have a random arrangement. Phenotypically, middle-transitional zone chondrocytes are spherical in shape. This zone also has the highest proteoglycan concentration of the zones. The collagen concentration in this zone is less than in the superficial-tangential zone. In the deep-radial zone, which accounts for about 30 percent of cartilage thickness, the proteoglycan and collagen concentration both diminish in concentration relative to the middle zone. The chondrocytes in the deep zone tend to form columns that are aligned with the radially oriented collagen fiber bundles which are perpendicular to the subchondral plate. These large fiber bundles insert across the tidemark, the boundary between uncalcified, or hyaline, cartilage and calcified cartilage, and securely anchor the cartilage to the bone. The calcified cartilage zone contains a low density of relatively small cells. One skilled in the art will understand that the forgoing illustration of the cartilage zones is not limiting, but merely exists as a conceptual tool to better understand cartilage structure. The biochemicals, histological, metabolic, biomechanical, and structural properties of cartilage are further discussed in Aydelotte et al., *Connect Tissue Res.*, 18:223-34 (1988); Aydelotte et al. *Connect Tissue Res.* 18:205-22 (1988); Aydelotte et al. *Am. J. Ther.* 3:3-8 (1996); Flannery et al. *Flannery Biochem. Biophys. Res. Commun.* 254:535-41 (1999); Hauselmann et al. *Arthritis Rheum.* 39:478-88 (1996); Pfister et al. *Biochem. Biophys. Res. Commun.* 286:268-73 (2001); Reid et al. *J. Orthop. Res.* 18:364-73 (2000); Schumacher et al. *Arch. Biochem. Biophys.* 311:144-52 (1994); and Schumacher et al. *J. Orthop. Res.* 17:110-20 (1999).

In this manner an artificial cartilage tissue is provided which physically and biologically mimics one or more characteristics of the structure and composition of articular cartilage and varies according to its depth from the joint surface. The present engineered cartilage provides distinct but continuous layers which are similar to the zones found in naturally occurring articular cartilage and can more readily replicate the characteristics of natural cartilage. For example, the engineered cartilage can have proteoglycan concentrations which increase from an outer surface of the tissue to a maximum amount in a middle area of the tissue and diminishes toward a deep layer of the tissue. Likewise, the outermost layer can contain cells, such as synovial cells and/or superficial-tangential chondrocytes, which secrete Del1 and/or Superficial Zone Protein (SZP) which is a major lubricant in cartilage tissue, thus mimicking the function of native cartilage.

The present invention also provides a method for producing a stratified, engineered cartilage tissue. One method for producing an engineered cartilage tissue of the present invention is shown in FIG. 1. According to this method, cartilage 10, which is generally attached to bone 12, is obtained and physically divided into two or more of a superficial-tangential section 14, middle-transitional section 16, deep-radial section 18 or a calcified cartilage section 20. Chondrogenic cells 22, 24 or 26 are obtained from their respective cartilage zone. For illustrative purposes only, cells 22 are obtained from superficial-tangential section 14, cells 24 are obtained from middle-transitional section 16 and cells 26 are obtained from deep-radial section 18. The chondrogenic cell numbers can optionally be increased to produce expanded chondrogenic cells 28, 30, and 32. The expanded chondrogenic cells 28, 30, and 32 are then optionally grown in, or on, a medium to produce chondrogenic cells with a cell-associated matrix specific to the chondrogenic cells being cultured 34, 36, and 38. As can be seen these steps are performed on cells 22, 24 and 26 without the mixing cells from the different cartilage zones. After the cells with their cell-associated matrix are obtained then cells and their cell-associated matrix 34, 36 and 38 are cultured together to form a unified and stratified cartilage tissue 40. Alternatively, one or more of the chondrogenic cells 22, 24, 26, 28, 30 or 32 can be cultured without cellular matrix to produce the stratified cartilage tissue 40. In particular, the cells making up a superficial zone 42 of the stratified cartilage can be cultured as monolayer without the production of extracellular matrix and laminated with the other cell layers as described above.

Preferred methods for culturing individual cartilage layers can be performed similar to the method described in U.S. Pat. No. 6,197,061 entitled "In vitro Production of Transplantable Cartilage Tissue, Cohesive Cartilage Produced Thereby, and Method for the Surgical Repair of Cartilage Damage" issued to Masuda et al. Generally, chondrogenic cells are isolated from the desired cartilage zone and are cultured to produce chondrocytes with a chondrogenic cell-associated matrix. The chondrocytes and their cell-associated matrix are then cultured on a semi-permeable membrane, preferably in the presence of one or more growth factors to produce an engineered cartilage tissue. Other suitable methods and techniques can be used in the present methods to optimize cell phenotype to a particular zone.

Isolation of Chondrocytes/Chondrogenic Cells

Chondrogenic cells useful in the present methods can be isolated from essentially any tissue containing chondrogenic cells having the desired phenotype. As used herein, the term "chondrogenic cell" is understood to mean any cell which, when exposed to appropriate stimuli, can differentiate into a cell capable of producing and secreting components characteristic of cartilage tissue. The chondrogenic cells can be isolated directly from pre-existing cartilage tissue, for example, hyaline cartilage, elastic cartilage, or fibrocartilage. Specifically, chondrogenic cells can be isolated from articular cartilage (from either weight-bearing or non-weight-bearing joints), costal cartilage, nasal cartilage, auricular cartilage, tracheal cartilage, epiglottic cartilage, thyroid cartilage, arytenoid cartilage and cricoid cartilage. Preferably, the chondrogenic cells are obtained from articular cartilage which has been divided into a superficial-tangential section, a middle-transitional section, a deep-radial section and a calcified cartilage section. These sections can be performed by first obtaining full depth articular cartilage and then physically separating the tissue into the appropriate sections, such as by using a cutting device.

Alternatively, chondrogenic cells can be isolated from bone marrow. See for example, U.S. Pat. Nos. 5,197,985 and 4,642,120, and Wakitani et al. *J. Bone Joint Surg.* 76:579-591 (1994). Chondrogenic cells can also be derived from stem cells, synovium, menisci, tendon, ligament or any other suitable source.

Suitable chondrocytes can be isolated from any suitable mammalian source organism, including, without limitation, human, orangutan, monkey, chimpanzee, dog, cat, rat, mouse, horse, cow, pig, and the like. Chondrocytes can be either isolated from sources having normal cartilage or cartilage which is known to be defective in some manner, such as having a genetic defect.

Chondrocyte cells used for preparation of the in vitro cell culture device of the present invention can be isolated by any suitable method. Various starting materials and methods for chondrocyte isolation are known (see generally, Freshney, Culture of Animal Cells: A Manual of Basic Techniques, 2d ed., A. R. Liss Inc., New York, pp. 137-168 (1987); Klagsburn, "Large Scale Preparation of Chondrocytes," *Methods Enzymol.* 58:560-564 (1979)).

If the starting material is a tissue in which chondrocytes are essentially the only cell type present, e.g., articular cartilage, the cells can be obtained directly by conventional collagenase digestion and tissue culture methods. Alternatively, the cells can be isolated from other cell types present in the starting material. One known method for chondrocyte isolation includes differential adhesion to plastic tissue culture vessels. In a second method, antibodies that bind to chondrocyte cell surface markers can be coated on tissue culture plates and then used selectively to bind chondrocytes from a heterogeneous cell population. In a third method, fluorescence activated cell sorting (FACS) using chondrocyte-specific antibodies is used to isolate chondrocytes. In a fourth method, chondrocytes are isolated on the basis of their buoyant density, by centrifugation through a density gradient such as Ficoll or Percoll.

It can be desirable in certain circumstance to utilize chondrocyte stem cells rather than differentiated chondrocytes. Examples of tissues from which stem cells for differentiation, or differentiated cells suitable for transdifferentiation, can be isolated include placenta, umbilical cord, bone marrow, skin, muscle, periosteum, perichondrium or adipose tissue. Cells can be isolated from these tissues by explant culture and/or enzymatic digestion of surrounding matrix using conventional methods.

Culture in Medium for the Production of Chondrocyte Cell-associated Matrix

Isolated chondrocytes/chondrogenic cells are suspended at a density of preferably at least about $10^4$ cells/ml in an appropriate medium, including reversible gels such as agarose or a solution of sodium alginate. A preferred method culturing the chondrocytes to produce the cell associated matrix is disclosed in Hauselmann et al., "Adult Human Chondrocytes Cultured in Alginate Form A Matrix Similar to Native Human Articular Cartilage", *Am. J. Physiol.* 271 (*Cell Physiol.* 40): C742-C752 (1996). The cells are cultured under conditions effective for maintaining their phenotypic conformation conducive to the production, upon the chondrocyte membrane, of a cell-associated matrix specific to the chondrogenic phenotype and similar to that found in vivo. Preferably, chondrocytes are cultured in alginate for at least about five days to allow for formation of a cell-associated matrix. The media within which the chondrocytes are cultured can contain a stimulatory agent, such as fetal bovine serum, to enhance the production of the cell-associated matrix.

In one embodiment, the chondrocytic cells are cultured in a growth medium, such as equal parts of Dulbecco's modified Eagle medium and Ham's F12 medium containing 20% fetal bovine serum (Hyclone, Logan, Utah), about 25 µg/ml ascorbate and antibiotic, such as 50 µg/ml gentamicin (Gibco). In an alternative approach, the chondrocytes are cultured in a closed chamber that allows for continuous pumping of medium. Preferably, the medium contains fetal bovine serum containing endogenous insulin-like growth factor-1 at a concentration of at least about 10 ng/ml. In this usage, fetal bovine serum can also be considered a growth factor. Suitable growth factors that can be exogenously added to the medium to maximally stimulate formation of the cell-associated matrix include but are not limited to osteogenic protein-1 (OP-1), bone morphogenic protein-2 and other bone morphogenetic proteins, transforming growth factor beta, and insulin-like growth factor.

In an alternative aspect of the invention, the culture medium for the chondrocytes can further include exogenously added specific growth factors. The addition of specific growth factors can act as an effective stimulator of matrix formation. Examples of growth factors include osteogenic protein-1, bone morphogenic protein-2, other bone morphogenetic proteins, transforming growth factor beta, and insulin-like growth factor and growth factors not already present in fetal bovine serum. In this aspect of the invention, growth factor is preferably added to the medium in an amount to near-maximally stimulate formation of the cell-associated matrix.

Preferably, amplification of chondrocytes or chondrogenic cells in the growth medium does not induce loss of the chondrocyte phenotype as occurs when amplification is performed in monolayer culture. Generally, chondrocyte phenotype refers to a cell that has (i) an appropriate shape and the ability to synthesize, secrete and/or accumulate within the matrix significant amounts of (ii) aggrecan and (iii) type II collagen corresponding to desired cartilage zone without (iv) accumulating within the matrix an appropriate amount of type I collagen. Chondrocytes cultured in alginate retain their phenotypic shape (typical of chondrocytes) and maintain a large amount of matrix. The matrix resembles hyaline cartilage histologically and is rich in aggrecan and collagen type II.

A phenotypically stable chondrocyte should also retain the ability to effectively incorporate the major macromolecules into a cartilage-like matrix. Normal chondrocytes can express small amounts of mRNA for collagen type I that they do not translate. Further, articular chondrocytes cultured in alginate for several months can synthesize some collagen type I molecules, but the latter never become incorporated into the forming matrix. Consequently, the appearance of small amounts of newly-synthesized collagen type I molecules in the medium does not necessarily denote the onset of dedifferentiation. Further, hyaluronan is not a marker of the chondrocytic phenotype since it is synthesized in large amounts by many other cell types. However, it is an important constituent of the cartilage matrix. Superficial chondrocytes phenotypically secrete superficial zone protein (SZP), are highly specialized and differ significantly from the middle zone or deep zone chondrocytes.

Cells that are phenotypically stable preferably synthesize at least about 10 times more aggrecan than collagen (on a mass basis). Further, the ratio of aggrecan to hyaluronan in the matrix preferably remains above about 10. The skilled artisan will recognize that phenotypic stability is different depending upon the type, e.g. superficial zone, middle zone or deep zone, of chondrocytes cultured and accordingly the amount of collagens, aggrecan, hyalouronan will vary depending upon the type of chondrocyte.

Chondrocyte with Cell-associated Matrix

Culture of chondrocytes in alginate results in the production of an ECM which is organized into two compartments: (i) a cell-associated matrix compartment which metabolically resembles the pericellular and territorial matrices of native tissues, and (ii) a further removed matrix compartment which metabolically resembles the interterritorial matrix of native tissue.

Although using chondorocytes that have a cell-associated matrix to produce a stratified cartilage is not required, the formation of a highly structured cell-associated matrix around each chondrocyte is desired for several reasons. First, the cell-associated matrix is anchored to the cell via receptors such as anchorin CII (which binds to collagen) and CD44 (which binds to hyaluronan in proteoglycan aggregates). Once this matrix has been reestablished, the cells are much less likely to become dedifferentiated. Second, the chondrocyte turns over proteoglycan aggrecan and thus remodels this matrix relatively rapidly. Additionally, the cell associated matrix is rich in (i) membrane bound resilient PGs and (ii) circular crosslinked collagen fibrils. As a consequence, the chondrocyte has its own protective shell, a shell that protects the cell from deformation. The chondrocyte is also generally less effective in remodeling the further removed matrix.

Preferably, the cell-associated matrix compartment of the ECM produced during culture in alginate includes aggrecan (the major cartilage proteoglycan), collagen types II, IX and XI, and hyaluronan as appropriate for the chondrogenic phenotype which produces the ECM. Aggrecan molecules are formed principally in aggregates bound to receptors (including CD44) on the chondrocyte cell membrane via hyaluronan molecules.

The relative proportions of each component in the cell-associated matrix vary depending on the length of time in culture. Preferably, homogenized cell-associated matrix, wherein all cartilage layers are assayed together, has at least about 5 mg/cc$^3$ of aggrecan, a ratio of aggrecan to hyaluronan (mg/mg) between 10:1 and 200:1, and a ratio of aggrecan to collagen (mg/mg) from 1:1 to about 10:1. Further, the molecular composition of the cell-associated matrix (around each cell) and further removed matrix (between the cells) can be altered by specific modifications of the culture conditions. These modifications involve the physical arrangement of the culture system and application of various growth factors. Manipulation of matrix production and organization are central to the engineering of articular cartilage in vitro for surgical treatment of cartilage injury.

Preferably, the contents of collagen and of the pyridinoline crosslinks of collagen increase with time of culture. The crosslinks in particular show a dramatic increase in concentration after two weeks of culture. By keeping the length of the culture period relatively short, the collagen fibrils in the cell-associated matrix do not become overly crosslinked. A tissue that has good functional properties but is relatively deficient in crosslinks is easier to manipulate. Tissues with higher amounts of crosslinking can be desired when more mature cartilage is sought to be simulated.

Recovery of Chondrocytes with Their Cell-associated Matrix

Preferably, recovery of chondrocytes with their cell-associated matrix is accomplished by solubilizing alginate gel after a sufficient culture period. Alginate gel is first solubilized using known techniques. The resulting cell suspension then is centrifuged, separating the cells with their cell-associated matrix in the pellet from the components of the further removed matrix in the supernatant.

Preferably, the above steps are performed in parallel for each of the chondrogenic phenotypes prior to culturing the layers together to form a cohesive cartilage tissue.

Culturing the Chondrocyte with their Cell-associated Matrix on a Semipermeable Membrane.

In this aspect of the invention, the chondrocytes with their cell-associated matrix, isolated as described above, are cultured in layers on a semipermeable membrane. Alternatively, one or more of the cell layers that lack a cell-associated matrix can be added to the culture to produce the cohesive cartilage tissue. Preferably, a cell culture insert is placed into a plastic support frame and culture medium flows around the cell culture insert. In this aspect, the cell culture insert includes a semipermeable membrane. The semipermeable membrane allows medium to flow into the cell culture insert in an amount effective for completely immersing the chondrocytes and their cell-associated matrix. In one embodiment the semipermeable membrane is chemically, enzymatically or biologically degradable. In another embodiment the cohesive, stratified cartilage tissue is removed from the semipermeable for further use.

Preferably, the semipermeable membrane allows the chondrocytes to have continuous access to nutrients while allowing the diffusion of waste products from the vicinity of the cells. In this aspect, the membrane should have a pore size effective to prevent migration of chondrocytes through the pores and subsequent anchoring to the membrane, preferably not be more than about 5 microns. Further, the membrane utilized should have a pore density effective for providing the membrane with sufficient strength so that it can be removed from its culture frame without curling, and with sufficient strength such that the tissue on the membrane can be manipulated and cut to its desired size. Preferably the membrane should have a pore density of at least about $8 \times 10^5$ pores/cm$^2$. The membrane can be made of any material suitable for use in culture. Examples of suitable membrane systems include but are not restricted to: (i) Falcon Cell Culture Insert Polyethylene terephthalate (PET) membrane, pore size 0.4 to 3 microns, diameter 12 to 25 mm]; (ii) Costaer Transwell Plate [Polycarbonate membranes, pore size, 0.1 to 5.0 microns, diameter 12 to 24.5 mm]; (iii) Nunc Tissue Culture Insert (Polycarbonate Membrane Insert: pore size, 0.4 to 3.0 microns, diameter 10 mm to 25 mm); Millicell Culture Plate Insert (PTFE (polytetrafluoroethylene) membrane, polycarbonate, pore size 0.4 to 3.0 microns, diameter 27 mm).

In another aspect of the invention, cells with their reestablished cell-associated matrix are further cultured in medium on the semipermeable membrane for an amount of time effective for allowing formation of a stratified cohesive cartilage matrix. Culture times will generally be at least about 3 days under standard culture conditions. Partial inhibition of matrix maturation prior to implantation can be important in providing a matrix that is not as stiff as mature cartilage, but which has enough tensile strength to retain its shape and structure during handling. In one embodiment, such a tissue should be malleable enough to be press fitted into a defect cartilage defect during surgical repair.

In producing the cohesive cartilage tissue, the chondrocytes, with or without cell-associated matrix, can be placed under different physical or biochemical conditions. In some embodiments, the cartilaginous tissue can be cultured under free swelling conditions. In other embodiments, the cartilage can be cultured under fluid flow, compressive (static or dynamic), shear conditions or combinations thereof. Additionally, the cartilage tissue can be cultured in a radially confined configuration, so that growth only occurs in the axial (thickness) direction. Mechanical properties of the cartilage matrix can also be controlled by increasing or decreasing the amount of time that the cartilage tissue is cultured on the membrane. Longer culture time will result in increased crosslink densities. Chondrocyte density in each of the layers can be varied as desired to reflect the cellularity of a replicated cartilage zone.

Cartilage Matrix

Preferably, in toto, the cartilage construct that forms on the semipermeable membrane has a concentration of aggrecan of at least about 5 $mg/cc^3$ and the cartilage matrix contains an amount of hyaluronan effective for allowing all the newly synthesized molecules to become incorporated into proteoglycan aggregates. The matrix of the tissue formed on the membrane contains aggregated aggrecan molecule at a concentration not less than 5 $mg/cc^3$, a ratio of aggrecan to hyaluronan of about 10:1 to about 200:1, and a ratio of aggrecan to collagen of about 1:1 to about 10:1. The engineered cartilage used in the present methods closely resembles naturally occurring articular cartilage in its physicochemical properties in a short period of time, typically about 14 days. It is also preferable to remove the engineered cartilage from the semipermeable membrane.

Generally, the engineered cartilage tissue will have a disklike structure conforming to the membrane; however, there is no requirement that the cartilage construct have a disk-like structure. In this aspect of the invention, the shape of the cartilage construct should be effective for allowing an orthopedic surgeon to handle the tissue (either a disk or sheet) and cut it into the size needed for a press fit into a defect. The size of the cartilage construct will generally be slightly bigger than the size of the defect. The engineered, stratified cartilage tissue of the present invention can then be surgically implanted into a cartilage defect as desired.

Another embodiment of the present invention provides methods of testing the effects of different test agents on engineered cartilage tissue. In the present methods, engineered cartilage tissue is exposed to one or more compounds (test agents) to determine what effect, if any, these compounds have on the growth, homeostatic balance and/or degradation of the cartilage tissue. The present culture system and methods are also useful for studying the anabolic and catabolic processes that are in balance in matrix homeostasis. In one method, engineered cartilage tissue is cultured to effectively mimic the physical properties and chemical and biological constituents of articular cartilage. The engineered cartilage tissue is used in a culture system to determine the effect of a test agent, alone or in combination with other agents, on the physical and chemical make-up of the engineered cartilage. As used herein, the term "test agent" is defined as a chemical compound that has no known modulating effect on the cartilage tissue at the stage of cartilage development in which the test agent is administered. Accordingly, one skilled in the art will understand that the term "test agent" is dependent on multiple factors including at least the compound to be tested and the developmental stage of the cartilage in which the compound is tested. Thus the same compound may be a test agent for one stage of cartilage development, such as culturing of chondrogenic cells to produce a cell-associated matrix, but not be a test agent for another stage of cartilage development because the compound has a known effect on that stage of cartilage development.

In the culture system, the engineered cartilage is contacted with a test agent. The test agent can be applied to the culture system in the presence or absence of known modulators which directly act on the cartilage tissue, including matrix metalloproteinases (MMPs) and serine proteases, or modulators which induce or inhibit these directly acting compounds, such as tissue inhibitors of metalloprotease (TIMPs), interleukin-1 receptor antagonist (IRAP), and cytokines tumor necrosis factor-$\alpha$. (TNF-$\alpha$) or interleukin-1 (IL-1). Likewise, the test agent can be applied to the culture system in the presence of one or more additional test agents to determine the effect the combination of agents has on the engineered cartilage. In a preferred embodiment, the test agent is not a known modulator of cartilage tissue, such as IL-1 and growth factors. Thus, the test agent can be a compound which acts (i) directly on the cartilage tissue, (ii) on a compound which acts directly on the cartilage tissue, or (iii) on a modulator of a compound which acts directly on the cartilage tissue.

Similarly, the test agent can be applied to the culture system at one or more of the various stages of the engineered cartilage lifecycle discussed above. For example, the test agent can be contacted with the isolated cells prior to, during or after: (i) chondrogenic cell culturing in growth medium to produce cell-associated matrix; (ii) recovery of the chondrocytes and the cell-associated matrix; (iii) culturing of the chondrocytes and cell-associated matrix to produce a stratified, cohesive engineered cartilage tissue; or (iv) the stratified, cohesive engineered cartilage tissue is obtained. In this manner, the test agent can be examined for activity in any or all of: (i) maintaining chondrogenic cell viability; (ii) maintaining chondrogenic cell phenotype; (iii) modulation of growth of the cell-associated matrix; (iv) modulation of cartilage matrix production and growth; (v) modulation of cartilage homeostasis or (vi) modulation of cartilage degradation.

Preferably, a control experiment is run for comparison so that the effect of the test agent can be more readily evaluated. Typically the control experiment will exclude the test agent, one or more of the combination of test agents, one or more compounds which act directly on the cartilage tissue or one or more modulators of compounds which act directly on the cartilage.

This embodiment lends itself to high throughput screening methods because testing of compounds can be completed in a relatively short amount of time. Likewise, large amounts of engineered cartilage tissue can be quickly obtained and small samples can be removed therefrom for sampling in multi-well plates, thus leading to easy automation of the instant screening methods. Because several tissue samples can be obtained from the same piece of engineered tissue, intraassay and interassay variability of data generated according to the present methods is very low. Significantly, the present methods can be economically achieved because the engineered cartilage can be cultured and tested in the same well of a multi-well plate, thus requiring little manipulation or perturbation of the tissue. Another significant advantage of the present method results from the fact that testing can be completed without the addition of extrinsic radioactivity, which is typically accomplished through the use of radioisotope labeling.

When non-radioactive techniques are used to quantify the engineered cartilage components after treatment with the test agent or modulators of cartilage tissue, it is preferable to digest the engineered cartilage matrix enzymatically. Enzymatic digestion of the cartilage matrix can be achieved using one or more proteases, such as papain, chymopapain, pronase and proteinase K. After enzymatic digestion, the proteoglycan content and DNA content of the cartilage can be measured using several well-known techniques in the art, such as the DMMB method and Hoechst 33258-dye method, respectively.

The present culture system can also be used to mimic different pathological states in cartilage tissue, including physical injury and disease states, such as rheumatoid arthritis. According to this embodiment cartilage is cultured and then either artificially injured, such as by physically cutting or tearing the engineered cartilage tissue, or treated with factors known to cause the progression of disease states, such as inflammatory factors and cartilage matrix degrading compounds. The engineered cartilage mimicking a pathological state can then be treated with one or more test agents as described above to determine the effect the test agent has on the pathological state. In this embodiment, as in others, it may be desirable to isolate chondrogenic cells that are known to have a certain defect, such as a genetic defect, or which have been genetically modified to produce a given defect.

After a test agent is identified as having a desired property, such as upregulating the production of cartilage, inhibiting cartilage degradation or enhancing cartilage degradation, the test agent can be identified and then either isolated or chemically synthesized to produce a therapeutic drug. Thus, the present methods can be used to make drug products useful for the therapeutic treatment of cartilage tissues in vitro and in vivo.

The present invention also provides kits for carrying out the methods described herein. In one embodiment, the kit is made up of instructions for carrying out any of the methods described herein. The instructions can be provided in any intelligible form through a tangible medium, such as printed on paper, computer readable media, or the like. The present kits can also include one or more reagents, buffers, culture media, culture media supplements, enzymes capable of degrading the engineered cartilage, chromatic or fluorescent dyes for staining or labeling a specific component of the cartilage tissue, radioactive isotopes for labeling specific components of the engineered cartilage, and/or disposable lab equipment, such as multi-well plates in order to readily facilitate implementation of the present methods. Examples of preferred kit components can be found in the description above and in the following examples.

The present methods or compositions can involve any or all of the steps or conditions discussed above in various combinations, as desired. Accordingly, it will be readily apparent to the skilled artisan that in some of the disclosed methods certain steps can be deleted or additional steps performed without affecting the viability of the methods.

This invention is further illustrated by the following non-limiting examples.

EXAMPLES

Experimental Protocol: Articular cartilage slices from the superficial (0-200 μm) and middle (400-1600 μm) zones were harvested from the femoropatellar groove of bovine calf knees (1-3 wk old, 6 animals). Superficial and middle zone chondrocyte subpopulations were isolated by sequential digestion for 1 hour with 0.2% pronase (Sigma-Aldrich, St. Louis, Mo.) and 12 hours with 0.025% collagenase P (Roche Diagnostics, Indianapolis, Ind.). Mok, et al., *J. Biol. Chem.* 269, 33021-7 (1994). Chondrocytes were suspended in 1.2% alginate (Keltone LV, Kelco, Chicago, Ill.) in 150 mM NaCl at $4 \times 10^6$ cells/ml, expressed from a 22 gauge needle into a 102 mM $CaCl_2$ solution to polymerize the alginate as small beads. Hauselmann, et al., *Matrix* 12, 116-29 (1992). The alginate beads were then transferred to a T-175 flask containing DMEM/F12 with additives (10% fetal bovine serum, 25 μg/ml ascorbate, 100 U/ml penicillin, 100 μg/ml streptomycin, 0.25 μg/ml Fungizone, 0.1 mM MEM non-essential amino acids, 0.4 mM L-proline, 2 mM L-glutamine) and cultured for 7 days with daily medium changes (1 ml per million cells). Cells and their associated matrix (CM) were released from alginate using 55 mM sodium citrate in 150 mM NaCl. Selected cells were labeled by incubating for 2 hours in medium containing 10 μM CellTracker™ Orange CMTMR (middle) or Green CMFDA (superficial) (Molecular Probes, Eugene, Oreg.). CM were then seeded onto 6.5 mm or 12 mm diameter cell inserts with a 0.4 μm pore size polyester membrane (Corning Inc., Corning, N.Y.) to achieve a final density of 5 million cells per $cm^2$ membrane area. S and M constructs were formed by seeding CM at one time, while S/M constructs were formed by seeding middle CM (2.5 million/$cm^2$) followed by superficial CM after a period of 18 hours to allow the initial layer to coalesce. All groups were incubated overnight prior to flooding the tissue culture well with medium. Constructs were cultured for 1 or 2 weeks with daily changes of medium (DMEM with additives). At the end of culture, constructs were removed from the membrane, measured for thickness with a current sensing micrometer, and weighed wet. Fluorescence and phase contrast photomicrographs were obtained at 1 week of sections with labeled cells and identical fields were overlayed using Adobe Photoshop (Adobe Systems, San Jose, Calif.) to visualize cell layering.

Biochemical analysis: Certain constructs (n=6-19 constructs per type per timepoint) were used for biochemical analyses. A 3 mm diameter punch was solubilized with proteinase K (Roche Diagnostics) and analyzed for DNA (Kim, et al., *Anal. Biochem.* 174, 168-76 (1988)), collagen as hydroxyproline (Woessner, J. F., *Arch. Biochem. Biophys.* 93, 440-7 (1961)) assuming 7.25 g collagen per g hydroxyproline, (Pal, S. et al., *Collagen Rel. Res.*, 1, 151-76 (1981)) and for sulfated GAG using the dimethylmethylene blue spectrophotometric assay. Farndale, et al., *Biochim. Biophys. Acta* 883, 173-7 (1986).

Mechanical testing: Other constructs (n=6-10 constructs per type per timepoint) were then transferred to a radially confining chamber with phosphate buffered saline (PBS) and subjected to a confined compression test to determine the equilibrium confined compressive modulus, $H_{A0}$. Chen, et al., *J. Biomechanics* 34, 1-12 (2001).

Immunohistochemistry: A third set of constructs were treated for 16 hours with 0.1 μM monensin (Sigma-Aldrich) in medium to prevent secretion of SZP from the Golgi apparatus, Schumacher, et al., *J. Orthop. Res.* 17, 110-20 (1999), frozen in O. C. T., and cut normal to the construct surface into 40 μm thick sections. Sections were probed for SZP and collagen II using the Vectastain ABC Elite Kit (Vector Laboratories, Burlingame, Calif.) per manufacturer's instructions, employing an anti-bovine SZP monoclonal antibody (mAb), 3-A-4, a mouse mAb anti-collagen II antibody cocktail (Chondrex, Redmond, Wash.), or mouse IgG (Vector Labs) as control. Sections were counterstained with methyl green (Vector Labs) for 2-5 minutes at room temperature and mounted in Crystal Mount (Biomeda, Foster City, Calif.). Serial sections were stained with 0.1% Alcian Blue in 0.4 M $MgCl_2$, 0.025 M sodium acetate, pH 5.6 to stain GAG. Aydelotte, et al., *Connect. Tissue Res.* 18, 223-34 (1988), Scott, et al., *Histochemie* 5, 221-33 (1965). Positive reactivity with SZP and collagen II, and GAG staining were documented by photomicroscopy using brightfield illumination. SZP positive and negative cells were marked using Adobe Photoshop and were counted in 200 μm bins starting from the free surface using calibrated images in NIH Image 1.62. As the constructs varied in thickness, counts between 400 μm deep, and 200 μm from the membrane surface were binned.

SZP ELISA: Individual samples (9-13 constructs per type) of pooled medium from days 12 to 14 of construct culture were allowed to bind to the wells of a 96 well plate overnight at 4° C. in PBS containing 0.1 M guanidine-HCl (Sigma-Aldrich), pH 7.4. Spent medium from superficial zone cartilage explant culture, which was standardized with purified SZP to a concentration of 22.5 μg/ml, was also assayed in two-fold dilutions to generate a sigmoidal control curve. Plates were washed extensively with PBS with 0.1% Tween-20 (Bio-Rad Laboratories, Hercules, Calif.) (PBS-T) and non-specific binding was blocked with 5% nonfat milk in PBS for 1 hour. Plates were washed, incubated for 1 hour with a 1:1000 dilution of mAb 3-A-4 in PBS with 0.1% bovine serum albumin (Sigma-Aldrich), washed, and incubated for an additional hour with a 1:1000 dilution of the same secondary antibody as above. ABTS substrate (Roche Diagnostics, Indianapolis, Ind.) was applied for 15 minutes and reaction was stopped by the addition of 1% SDS in water. Optical density (OD) measurements were made at 405 nm on an EMAX microplate reader (Molecular Devices, Menlo Park, Calif.). Three dilutions were used to calculate the equivalent neat OD, based on a least-squares sigmoidal fit, which was then converted to SZP concentration using the control curve.

Western Blot: Pooled medium from days 12 to 14 of construct culture (5 constructs per type) and purified SZP were digested with chondroitinase ABC (Seikagaku America, Rockville, Md.) in sample buffer (0.1 M Tris and 0.05 M sodium acetate, pH 8.0) for 2 hours at 37° C. Samples were mixed with an equal volume of 2× Laemmli sample buffer and boiled for 3 minutes immediately prior to electrophoresis on a 5% SDS-polyacrylamide gel. Separated proteins were transferred to an Immobilon-P membrane (Millipore, Burlington, Mass.) overnight at 4° C. with 250 mA in a transfer buffer containing 12 mM Tris, 0.3 mM EDTA, and 6 mM sodium acetate, pH 7.4. The membrane was then removed and blocked for 30 minutes with 5% nonfat dry milk (Nestle Food Company, Glendale, Calif.) in PBS-T. After rinsing, the membrane was incubated for 1 hour with mAb 3-A-4 diluted 1:200 in PBS-T, followed by incubation with a horseradish peroxidase conjugated goat-anti-mouse IgG (Pierce, Rockford, Ill.) secondary antibody (1:1000) for 2 hours. The proteins were visualized with hyperfilm-ECL (Amersham Pharmacia, Piscataway, N.J.). The approximate molecular weight of the SZP bands was determined using the rainbow molecular weight standards.

Statistical Analysis: Data are expressed as mean ± SEM. The effects of construct type and culture duration were assessed by ANOVA using Systat 5.2.1 (Systat Software, Inc., Richmond, Calif.), with Tukey post-hoc tests, where appropriate.

Experimental Results

Figure 2:
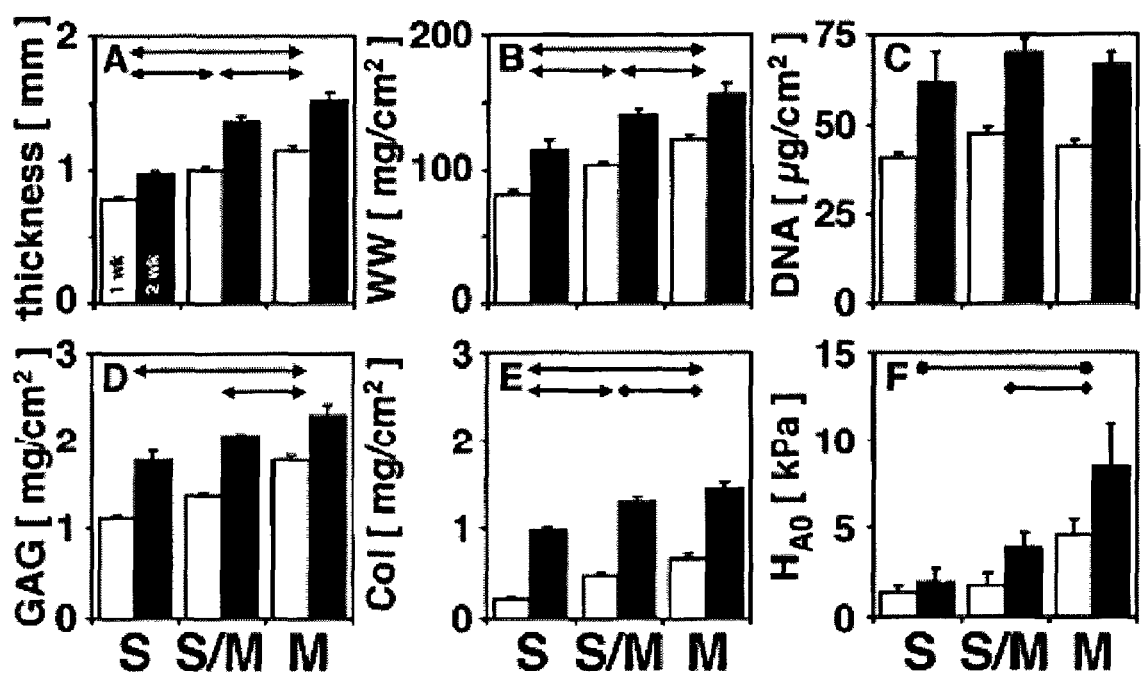
FIG. 2 demonstrates the structural, compositional, and functional properties of three types of cartilage constructs formed from superficial and/or middle zone chondrocytes after 1 week and 2 weeks in culture as set forth in the examples. Wet weight (WW), DNA, GAG, and collagen were all normalized to the cross sectional area of the construct. Data are expressed as mean ± SEM ($p<0.001$ (♦), $p<0.01$ (●), $p<0.05$ (♦)).

Cohesive cartilage constructs were fabricated from chondrocytes, isolated separately from superficial and middle zones of bovine calf cartilage, using the alginate recovered chondrocyte method. Masuda, K. et al. *International Symposium on Molecular Cell Biology of Cartilage Development and Repair* 70 (1999). Three construct types were formed: homogeneous superficial (S), homogeneous middle (M), and stratified with superficial layered atop middle (S/M) (FIG. 1). Distinct cell layers were created and maintained in S/M constructs, as demonstrated by localization of fluorescently-labeled superficial and middle zone cells (data not shown). Construct thickness varied with construct type ($p<0.001$) and increased with culture duration ($p<0.001$), with M constructs being significantly thicker than S/M constructs, which were in turn thicker than S constructs after 1 and 2 weeks of culture (FIG. 2A). Construct wet weight varied in a manner consistent with thickness data (FIG. 2B). Cell proliferation was also evident, as DNA content increased from 1 to 2 weeks ($p<0.01$), but was similar in all constructs ($p=0.12$) (FIG. 2C).

Cartilage matrix molecules, collagen and GAG, were deposited at different rates by the various types of constructs. Collagen content tripled from 1 to 2 weeks ($p<0.001$) and was significantly greater in M than S constructs ($p<0.001$), and at an intermediate level in S/M constructs ($p<0.001$ to S, $p<0.05$ to M) (FIG. 2E). GAG content followed similar trends (FIG. 2D), but was more abundant than collagen, and increased 51% from 1 to 2 weeks ($p<0.001$). The equilibrium confined compressive modulus increased with time, although not significantly ($p=0.06$), and was greater in M constructs than S ($p<0.01$) and S/M constructs ($p<0.05$) (FIG. 2F).

Figure 3:
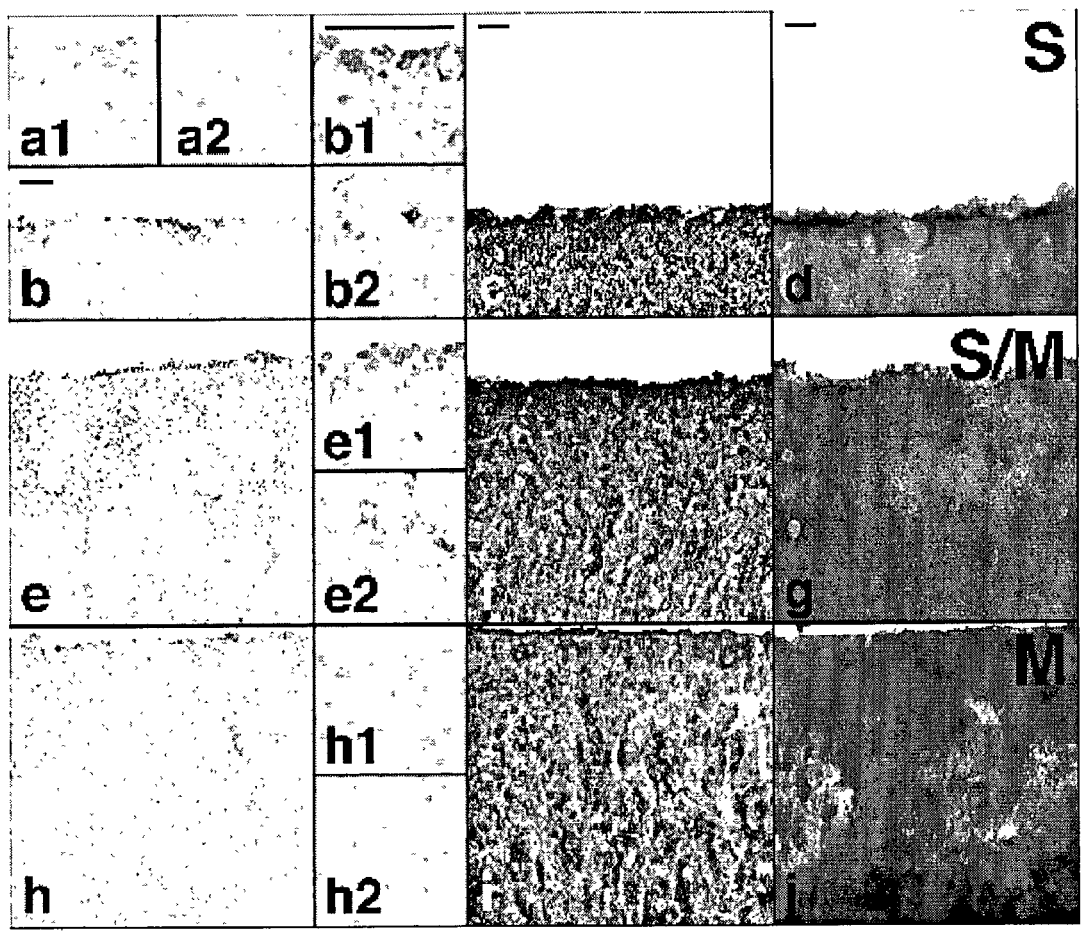
FIG. 3 shows the localization of secreted and matrix molecules in 2-week S, S/M, and M cartilage constructs. Sections were treated with mouse IgG control (a), or immunostained for SZP (b,e,h) or for collagen II (c,f,i) with methyl green counterstain. Higher power images of selected regions from the top (1), middle (2) of each construct are shown for clarity. GAG (d,g,j) was detected histochemically with Alcian Blue. Bar=100 μm.

Collagen type II, which is used as a marker of hyaline cartilage, was strongly detected throughout the thickness of all types of constructs by immunohistochemistry (FIGS. 3c,f, i). GAG (specifically chondroitin sulfate and keratan sulfate) was visualized on construct sections using Alcian Blue dye. Similar to collagen II, GAG was present throughout the thickness of all sections (FIGS. 3d,g,j). Staining was heavier in the inferior portion of the S/M constructs (FIG. 3j).

Figure 4:
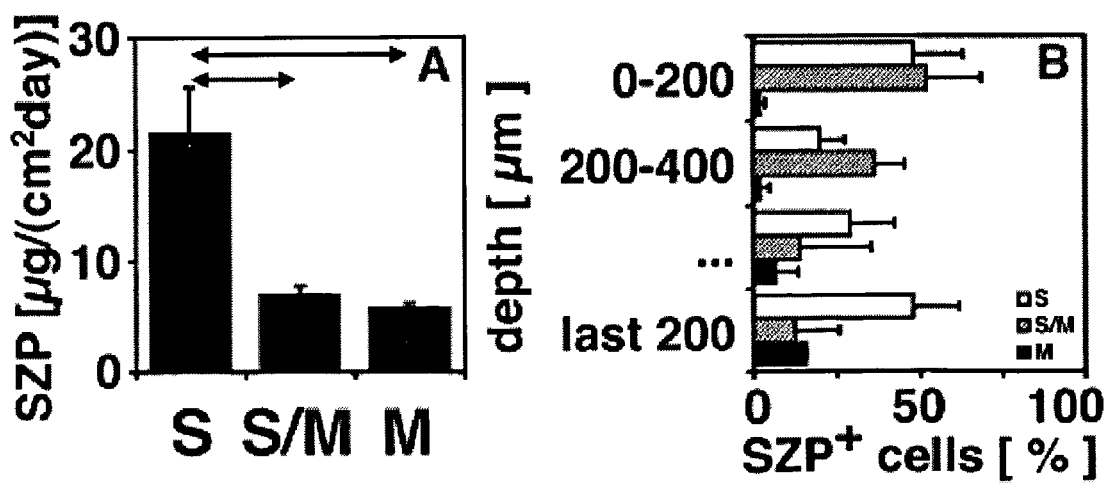
FIG. 4 shows the superficial zone protein measured in spent culture media pooled from days 12 to 14 of construct culture by indirect ELISA ($p<0.001$ (♦) (A), and the depth-dependent SZP expression in each construct type after 2 weeks of culture as measured by immunocytochemistry (B).

SZP, a secreted molecule that is not retained in the matrix, was detected intracellularly by immunohistochemistry in constructs treated with monensin. SZP was immunolocalized inside a high proportion of the chondrocytes in S and S/M constructs, but in very few chondrocytes within M constructs (FIGS. 3b, e, h). Cells near both surfaces of S constructs stained more intensely than cells of the interior, while cells at the free surface stained more intensely than other cells in S/M constructs. This pattern of SZP expression in S/M constructs resembled the steep monotonic gradient of SZP positive cells in native calf cartilage. After 2 weeks of culture, the percentage of SZP positive cells was 52±15% in the top 200 μm, whereas the next 200 μm was 36±8%, and was only 13±14% in the remainder of the tissue (FIG. 4B). However, S constructs showed similar levels at both surfaces (48±16% top 200 μm, and 48±14% bottom 200 μm) and lower levels in the interior (20±9% 200-400 μm, 29±21% remainder of tissue) (FIG. 4B). M constructs had low levels of SZP positive cells throughout, ranging from 2±2% in the top 200 μm to 15±0% in the bottom 200 μm (FIG. 4B).

When analyzed by Western blot, the SZP in media pooled from days 12-14 of culture had the same electrophoretic mobility as purified SZP, with an approximate molecular weight of ~345 kD. The amount of SZP in each pool was quantified by ELISA. S constructs secreted 21.5±4.0 μg/[cm$^2$*day], which was three to four-fold more SZP per day than both S/M and M constructs (p<0.001) (FIG. 4A).

Discussion of Results

The above results indicate that chondrocyte subpopulations can play an important role in determining the structure, composition, metabolism, and mechanical function of tissue engineered cartilage. Constructs formed from superficial zone chondrocytes had relatively lower matrix content and compressive properties than constructs formed from middle zone chondrocytes. Additionally, when superficial and middle zone cells were combined in a layered fashion, the tissue developed intermediate matrix properties and SZP localization similar to native cartilage, with the greatest SZP secretion from only a few cell layers of the superficial zone.

These in vitro studies with stratified constructs have recapitulated a fetal-like cartilage, with high cellularity, SZP stratification, and a low compressive modulus. This tissue that mimics immature cartilage can be preferred for use as a biological implant. Young cartilage, when injured, has been shown to heal, Namba, et al. *J. Bone Joint Surg.* 80-A, 4-10 (1998), whereas adult cartilage does not and integrates poorly with biological grafts. Hunter, W. Philos. Trans. R. Soc. London 42, 514-21 (1743) and DiMicco, et al. *Osteoarthritis Cartilage* (in press), (2001). Engineered cartilage with immature mechanical properties has also shown greater integration potential than engineered cartilage with more fully-developed matrix properties. Also, the greater growth potential of young cartilage may allow for more complete filling of a defect with irregularities.

While chondrocyte subpopulations may differentiate in vitro and after implantation into a defect site, supplying cells with proper zonal phenotype to their respective zones in engineered tissue can reduce the time of tissue maturation by reducing the need for cellular migration and/or differentiation in the tissue. In this study, the number of SZP expressing cells in S constructs declined with culture duration, yet the overall production of SZP increased, indicating a phenotypic switch and complex regulation of SZP production. Cells near the surfaces of these constructs remained positive over the culture period, while the percentage of SZP positive cells on the interior declined. This could suggest a phenotypic dependence on nutrient levels or gradients in the tissue, as are established in vivo, due to the avascular nature of cartilage. Alternately, SZP expression could be inhibited by cell-cell or, more likely, cell-matrix interactions. The layering scheme described herein has localized the cells in their proper zones and maintained the phenotypic expression pattern.

An engineered construct with stratification that mimics native cartilage may be particularly useful for repair of cartilage defects in the future. By providing a functional superficial zone at the time of implantation, wear on the surface of the implant may be reduced due to the production of protective and lubricating molecules. Flannery, C. R. et al. *Biochem. Biophys. Res. Commun.* 254, 535-41 (1999). Additionally, the lubricating effects of SZP may play an inhibitory role in integration, and thus may not be desirable below the articular surface at the host-graft interfaces. Rather, matrix elaborating middle and deep zone chondrocytes could provide both the stiffness necessary to bear load, and matrix molecules such as collagen which have been implicated as key players in cartilage integration. DiMicco, et al. *J. Orthop. Res.* 19, 1105-12 (2001).

Based on the experimental results, methods to produce a tissue with a layer containing SZP-expressing cells atop a layer of SZP-negative cells have been established.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

All references disclosed herein are specifically incorporated herein by reference thereto.

While preferred embodiments have been illustrated and described, it should be understood that changes and modifications can be made therein in accordance with ordinary skill in the art without departing from the invention in its broader aspects as defined in the following claims.

What is claimed is:

1. A cultured, stratified cartilage tissue construct which is malleable such that it may be press fitted into a cartilage defect during surgical repair, said construct consisting essentially of at least two cartilage layers selected from the group consisting of:
    (i) a cartilage layer having chondrogenic cells wherein the chondrogenic cells consist essentially of chondrogenic cells having a chondrocytic phenotype corresponding to chondrocytes present in the superficial-tangential zone of natural cartilage, wherein the layer is formed by culturing said cells in an alginate medium such that the cells form a cell-associated matrix, and dissociating the cells together with the cell-associated matrix from the alginate to produce the cartilage layer;
    (ii) a cartilage layer having chondrogenic cells wherein the chondrogenic cells consist essentially of chondrogenic cells having a chondrocytic phenotype corresponding to chondrocytes present in the middle-transitional zone of natural cartilage, wherein the layer is formed by culturing said cells in an alginate medium such that the cells form a cell-associated matrix, and dissociating the cells together with the cell-associated matrix from the alginate to produce the cartilage layer; and
    (iii) a cartilage layer having chondrogenic cells wherein the chondrogenic cells consist essentially of chondrogenic cells having a chondrocytic phenotype corresponding to chondrocytes present in the deep-radial zone of natural cartilage, wherein the layer is formed by culturing said cells in an alginate medium such that the cells form a cell-associated matrix, and dissociating the cells together with the cell-associated matrix from the alginate to produce the cartilage layer;
wherein the construct is formed by associating the at least two layers into a stratified cohesive cartilage construct.

2. The cultured, stratified cartilage tissue construct of claim 1, wherein the chondrogenic cells present in each of the at least two cartilage layers are obtained from the natural cartilage zone to which their chondrocytic phenotype corresponds.

3. The cultured, stratified cartilage tissue construct of claim 1, wherein the construct consists essentially of:
  (i) the cartilage layer having chondrogenic cells wherein the chondrogenic cells consist essentially of chondrogenic cells having a chondrocytic phenotype corresponding to chondrocytes present in the superficial-tangential zone of natural cartilage; and
  (ii) the cartilage layer having chondrogenic cells wherein the chondrogenic cells consist essentially of chondrogenic cells having a chondrocytic phenotype corresponding to chondrocytes present in the middle-transitional zone of natural cartilage.

4. The cultured, stratified cartilage tissue construct of claim 1, wherein the construct consists essentially of:
  (i) the cartilage layer having chondrogenic cells wherein the chondrogenic cells consist essentially of chondrogenic cells having a chondrocytic phenotype corresponding to chondrocytes present in the superficial-tangential zone of natural cartilage;
  (ii) the cartilage layer having chondrogenic cells wherein the chondrogenic cells consist essentially of chondrogenic cells having a chondrocytic phenotype corresponding to chondrocytes present in the middle-transitional zone of natural cartilage; and
  (iii) the cartilage layer having chondrogenic cells wherein the chondrogenic cells consist essentially of chondrogenic cells having a chondrocytic phenotype corresponding to chondrocytes present in the deep-radial zone of natural cartilage;
wherein layer (i) is adjacent to layer (ii), and layer (ii) is adjacent to layer (iii).

5. The cultured, stratified cartilage tissue construct of claim 1, wherein the construct consists essentially of:
  (i) the cartilage layer having chondrogenic cells wherein the chondrogenic cells consist essentially of chondrogenic cells having a chondrocytic phenotype corresponding to chondrocytes present in the superficial-tangential zone of natural cartilage; and
  (iii) the cartilage layer having chondrogenic cells wherein the chondrogenic cells consist essentially of chondrogenic cells having a chondrocytic phenotype corresponding to chondrocytes present in the deep-radial zone of natural cartilage.

6. The cultured, stratified cartilage tissue construct of claim 1, wherein the construct is not supported by a solid support.

7. The cultured, stratified cartilage tissue construct of claim 1, wherein the cell-associated matrix present in each of the two or more cartilage layers is produced by the chondrogenic cells in the layer, and correspond in phenotype to the cartilage matrix present in the corresponding natural cartilage zone.

8. The cultured, stratified cartilage tissue construct of claim 7, wherein the cell-associated matrix corresponds in phenotype to immature or mature cartilage matrix present in the corresponding natural cartilage zone.

9. The cultured, stratified cartilage tissue construct of claim 1, wherein at least one of the at least two cartilage layers is:
  (iii) a cartilage layer having chondrogenic cells wherein the chondrogenic cells consist essentially of chondrogenic cells having a chondrocytic phenotype corresponding to chondrocytes present in the superficial-tangential zone of natural cartilage, wherein the layer is formed by culturing said cells in an alginate medium such that the cells form a cell-associated matrix, and dissociating the cells together with the cell-associated matrix from the alginate to produce the cartilage layer;
wherein the chondrogenic cells have a chondrocytic phenotype corresponding to chondrocytes present in the superficial-tangential zone of natural cartilage which secrete superficial zone protein.

10. A method of producing the cultured, stratified cartilage tissue construct of claim 1, comprising:
  (a) associating at least two cartilage layers into a stratified cohesive cartilage construct wherein each cartilage layers is selected from the group consisting of:
    (i) a cartilage layer having chondrogenic cells wherein the chondrogenic cells consist essentially of chondrogenic cells having a chondrocytic phenotype corresponding to chondrocytes present in the superficial-tangential zone of natural cartilage , wherein the layer is formed by culturing said cells in an alginate medium such that the cells form a cell-associated matrix, and dissociating the cells together with the cell-associated matrix from the alginate to produce the cartilage layer;
    (ii) a cartilage layer having chondrogenic cells wherein the chondrogenic cells consist essentially of chondrogenic cells having a chondrocytic phenotype corresponding to chondrocytes present in the middle-transitional zone of natural cartilage wherein the layer is formed by culturing said cells in an alginate medium such that the cells form a cell-associated matrix, and dissociating the cells together with the cell-associated matrix from the alginate to produce the cartilage layer; and
    (iii) a cartilage layer having chondrogenic cells wherein the chondrogenic cells consist essentially of chondrogenic cells having a chondrocytic phenotype corresponding to chondrocytes present in the deep-radial zone of natural cartilage wherein the layer is formed by culturing said cells in an alginate medium such that the cells form a cell-associated matrix, and dissociating the cells together with the cell-associated matrix from the alginate to produce the cartilage layer.

11. The method of claim 10, wherein the cell-associated matrix of each layer correspond in phenotype to the cartilage matrix present in the natural cartilage zone with which the chondrogenic cells have a corresponding chondrocytic phenotype.

12. The method of claim 10, wherein the chondrogenic cells are cultured in the alginate medium on a semi-permeable membrane.

13. The method of claim 10, wherein the chondrogenic cells are cultured in the presence of a growth factor.

14. The method of claim 10, wherein the chondrogenic cells are isolated from the natural cartilage zone to which their chondrocytic phenotype corresponds.

15. The method of claim 10, wherein the at least two cartilage layers associated in step (a) are:
  (i) the cartilage layer having chondrogenic cells wherein the chondrogenic cells consist essentially of chondrogenic cells having a chondrocytic phenotype corresponding to chondrocytes present in the superficial-tangential zone of natural cartilage; and
  (ii) the cartilage layer having chondrogenic cells wherein the chondrogenic cells consist essentially of chondrogenic cells having a chondrocytic phenotype corresponding to chondrocytes present in the middle-transitional zone of natural cartilage.

16. The method of claim 10, wherein the at least two cartilage layers associated in step (a) are:
- (ii) the cartilage layer having chondrogenic cells wherein the chondrogenic cells consist essentially of chondrogenic cells having a chondrocytic phenotype corresponding to chondrocytes present in the middle-transitional zone of natural cartilage; and
- (iii) the cartilage layer having chondrogenic cells wherein the chondrogenic cells consist essentially of chondrogenic cells having a chondrocytic phenotype corresponding to chondrocytes present in the deep-radial zone of natural cartilage.

17. The method of claim 10, wherein the at least two cartilage layers associated in step (a) are:
- (i) the cartilage layer having chondrogenic cells wherein the chondrogenic cells consist essentially of chondrogenic cells having a chondrocytic phenotype corresponding to chondrocytes present in the superficial-tangential zone of natural cartilage;
- (ii) the cartilage layer having chondrogenic cells wherein the chondrogenic cells consist essentially of chondrogenic cells having a chondrocytic phenotype corresponding to chondrocytes present in the middle-transitional zone of natural cartilage; and
- (iii) the cartilage layer having chondrogenic cells wherein the chondrogenic cells consist essentially of chondrogenic cells having a chondrocytic phenotype corresponding to chondrocytes present in the deep-radial zone of natural cartilage.

18. The method of claim 10, further comprising:
- (b) surgically implanting the cultured, stratified cartilage tissue construct into a joint.

* * * * *